US011253658B2

(12) United States Patent
Montagnino et al.

(10) Patent No.: US 11,253,658 B2
(45) Date of Patent: Feb. 22, 2022

(54) PERSONAL INHALING DEVICE (71) Applicants: James G Montagnino, Saint Charles, IL (US); Dirk Niedermann, Chicago, IL (US); Li Kin Wan, Fanling (HK); Chan Ming Hon, Tseung Kwan O (HK)

(72) Inventors: James G Montagnino, Saint Charles, IL (US); Dirk Niedermann, Chicago, IL (US); Li Kin Wan, Fanling (HK); Chan Ming Hon, Tseung Kwan O (HK)

( * ) Notice: Subject to any disclaimer, the term of this patent is extended or adjusted under 35 U.S.C. 154(b) by 817 days.

(21) Appl. No.: 15/984,351

(22) Filed: May 19, 2018

(65) Prior Publication Data
US 2019/0351155 A1 Nov. 21, 2019

(51) Int. Cl.
A61M 11/00 (2006.01)
A61M 11/04 (2006.01)
A61F 7/00 (2006.01)

(52) U.S. Cl.
CPC ......... *A61M 11/005* (2013.01); *A61F 7/0085* (2013.01); *A61M 11/042* (2014.02); *A61F 2007/0062* (2013.01); *A61F 2007/0064* (2013.01); *A61F 2007/0086* (2013.01); *A61F 2007/0087* (2013.01); *A61M 2205/3334* (2013.01); *A61M 2205/3368* (2013.01); *A61M 2205/3379* (2013.01); *A61M 2205/584* (2013.01); *A61M 2205/587* (2013.01);
(Continued)

(58) Field of Classification Search
CPC .......................... A61M 11/00; A61M 11/005; A61M 15/0085; A61F 7/0085; B05B 17/00; B05B 17/04; B05B 17/06; B05B 17/0607; A61H 33/06; A61H 33/12
See application file for complete search history.

(56) References Cited

U.S. PATENT DOCUMENTS 3,707,971 A * 1/1973 Yamamoto ............. A61H 33/06
607/84
3,949,743 A * 4/1976 Shanbrom ............... A61H 33/12
128/200.14
(Continued)

FOREIGN PATENT DOCUMENTS

JP 2016077598 A * 5/2016

OTHER PUBLICATIONS

Vicks, "Sinus Inhaler Personal Steam Inhaler Use and Care Manual", Mar. 7, 2017 (Year: 2017).*
(Continued)

Primary Examiner — Michael J Tsai
Assistant Examiner — Ned T Heffner
(74) Attorney, Agent, or Firm — Steven Ivy P.C.

(57) ABSTRACT

A personal inhaling apparatus is provided. The apparatus includes an ultrasonic personal inhaler with ultra-fine mist transducer that delivers both cool and warm mist using a heater, a face mask, a fluid supply means, and a power source including batteries and/or corded power supply. The apparatus may include a receptacle for a scented pad placed in contact with the heater. Indicators functioning in a pre-determined manner provide indication on if the device is delivering a cool mist, a warm mist, is switched-OFF, a level of charge of a power source, and a level of the fluid in the fluid supply means.

12 Claims, 7 Drawing Sheets (52) U.S. Cl.
CPC ............... *A61M 2205/8206* (2013.01); *A61M 2205/8262* (2013.01)

(56) References Cited

U.S. PATENT DOCUMENTS

| | | | | |
|---|---|---|---|---|
| 4,300,556 | A | * | 11/1981 | Ochi ..................... A61H 35/008 604/291 |
| 5,749,359 | A | * | 5/1998 | Hansen ................ A62B 18/006 128/205.25 |
| 2004/0025242 | A1 | * | 2/2004 | Leung ................... A61H 33/12 4/524 |
| 2009/0133645 | A1 | * | 5/2009 | Yao ....................... A61H 33/12 122/407 |
| 2009/0287142 | A1 | * | 11/2009 | Miyake ................ A61L 2/0011 604/22 |
| 2012/0112371 | A1 | * | 5/2012 | Kanel ...................... F24F 6/02 261/28 |
| 2013/0099025 | A1 | * | 4/2013 | McDonnell ......... B05B 17/0607 239/589 |
| 2013/0102937 | A1 | * | 4/2013 | Ehrenreich ........ A61H 23/0236 601/47 |
| 2016/0143771 | A1 | * | 5/2016 | Swyer ................... A61F 7/0085 607/104 |
| 2016/0192760 | A1 | * | 7/2016 | Nishiura ................ A61M 11/06 239/337 |
| 2016/0360917 | A1 | * | 12/2016 | Richardson ........... A47J 31/005 |
| 2017/0072085 | A1 | * | 3/2017 | Gruenbacher .......... A61L 9/127 |
| 2018/0078729 | A1 | * | 3/2018 | Niedermann ....... A61M 16/109 |

OTHER PUBLICATIONS

"The benefits of steaming face for glowing and healthy skin", My Awesome Beauty, archived Jan. 26, 2018 (Year: 2018).*

Secura, "Table top Warm & Cool Mist Ultrasonic Facial Steamer", 2010 (Year: 2010).*

* cited by examiner

PERSONAL INHALING DEVICE

FIELD OF INVENTION

The present invention is generally related to an inhaling device, and more particularly related to an ultrasonic warm and cool mist personal inhaling device.

BACKGROUND

A variety of inhaling devices are available in the market. One kind of inhaler, i.e., a steam inhaler is generally available as a table top inhaler or a hand-held inhaler. Generally, the table top inhalers may be limited by the length of the cord, making them not portable. User safety precautions are necessary to prevent injury due to spilling boiling water on the user if not properly handled leading to the inhalers being used as a counter or table top device. The hand-held steam inhaler devise may also be cord restricted thus making them less-portable. Moreover, steam inhalers typically provide a warm mist output (steam requires boiling water). Cool mist inhalers using ultrasonic generated mist can only produce a cool vapor and many are battery operated and used as facial coolers when the user is in a high heat environment.

Therefore, there exists a need to provide an improved personal inhaling/cooling device that is more portable and provide a user with both warm and cool mists as needed.

SUMMARY OF THE INVENTION

Hence, it is an objective of the present invention to provide an apparatus for inhaling that comprises a warm mist and cool mist generator vapor. In one embodiment, the apparatus incorporates ultrasonic production of both a warm mist and a cool mist.

It is further an objective of the present invention to provide a uniform ultra fine water/moisture particle size for inhalation using the personal inhaling device.

It is another objective of the present invention to add provisions in the inhaling device for adding customized scented pads for better aromatic results.

It is another objective of the present invention to add provisions for indicating in a pre-determined manner if the device is delivering a cool mist, a warm mist, is switched-OFF, a level of charge of a power source, and a level of the fluid in the fluid supply means.

In one embodiment is provided a personal inhaling apparatus. The apparatus includes an ultrasonic personal inhaler with ultra-fine mist transducer that delivers both cool and warm mist using low voltage AC to DC corded adapter or operated with rechargeable DC batteries or as a battery only devise using disposable batteries or rechargeable batteries or a devise that operates off a low voltage AC to DC adapter with no batteries. The apparatus also includes a means for providing a warm mist in a hot mode of the device, the means comprising a heating system in a tube form attached to the ultra-fine mist transducer, the ultrafine sonic transducer in combination with the heater warming the exit mist of the transducer from fluid provided by a fluid supply means in the device to form a heated warm mist in a hot mode of the device. A vented face mask is attached to the tubular heater for pulling in a cold air stream from surrounding environment to surround the heated warm mist thus maintaining temperature level and moisture level of the exiting mist and a means for providing a scented exiting mist comprising a receptacle for a scented pad in contact with the heating system in tube form is also included. The scent pad releases its scent when heated. The exiting air vapor steam velocity in conjunction with the cool air sucked into the exiting stream of vapor pulls the scent into the exiting ultrafine mist. The apparatus includes a means for providing a cool mist in a cool mode of the device, the means comprising an ultra-fine mist transducer forming a cool mist from fluid provided by the fluid supply means in the device. Indicators functioning in a pre-determined manner provide indication on if the device is delivering a cool mist, a warm mist, is switched-OFF, a level of charge of a power source, and a level of the fluid in the fluid supply means.

In another embodiment, is provided a personal inhaling device. The device may include a face mask. The face mask comprises a vented face mask. The device also includes an ultrasonic transducer and a heater. The ultrasonic transducer in combination with the heater is capable of warming an exiting mist from a reservoir in the device to form a heated warm mist; and the face mask is designed to pull in a cold air stream to surround the heated warm mist. A receptacle may be placed directly over the heater to accept a scented pad, and a scent from the scented pad in the receptacle in contact with the heater is released into the exiting heated warm mist. The device may also include a slot below the heater to collect condensed vapors.

In another embodiment is provided a method. The method includes a step of providing a device. The device is a personal portable inhaling device. The device includes a power source and a switch, wherein the switch is used to turn the device to a switch ON position or a switch OFF position. The switch ON position the device is activated to function in a plurality of modes, wherein the plurality of modes comprises a cool mode and a hot mode. The method also provides a means for adjusting flow rates in the cool mode of the personal inhaler device. The means comprises pressing a second portion of the switch once to provide a low temperature and a low output warm mist; wherein the means comprises pressing a second portion of the switch twice to provide a higher temperature and a high output warm mist; wherein the means comprises pressing a second portion of the switch thrice to turn the device to the switch OFF position; and wherein the method is for inhaling using the personal inhaler device, wherein the means comprises pressing a first portion of the switch once to provide a low output cool mist; wherein the means comprises pressing a first portion of the switch twice to provide a high output cool mist; wherein the means comprises pressing a first portion of the switch thrice to turn the device to the switch OFF position; and wherein the method is for inhaling using the personal inhaler device.

In another embodiment is provided a personal inhaling device. The device includes a face mask, wherein the face mask comprises a vented face mask; an ultrafine sonic transducer; a heater; a reservoir; wherein a liquid for forming a mist is stored in the reservoir; a rechargeable power source; a switch, wherein the switch is used to turn the device to a switch ON position or a switch OFF position. In the switch ON position the device is activated to function in a plurality of modes, wherein the plurality of modes comprises a cool mode and a hot mode. In the switch ON position the cool mode is activated by pressing a first portion of the switch; and wherein in the switch ON position the hot mode is activated by pressing a second portion of the switch; and wherein the switch ON position in the cool mode, switch ON position in the hot mode, the switch OFF position, a level of charge of the power source, a level of the liquid in the reservoir, are indicated in a pre-determined manner using indicators in the device.

The foregoing and other objects, features and advantages of the invention will be apparent from the following more particular descriptions of exemplary embodiments of the invention.

BRIEF DESCRIPTION OF THE DRAWINGS

The manner in which these objectives and other desirable characteristics can be obtained is explained in the following description and attached figures in which like reference numerals refer to similar elements and in which.

DETAILED DESCRIPTION

This patent describes the subject matter for patenting with specificity to meet statutory requirements. However, the description itself is not intended to limit the scope of this patent. The principles described herein may be embodied in many different forms, while being used individually or jointly.

Illustrative embodiments of the invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

The present invention discloses an apparatus/a device and related method for steam inhalation. The device may be used by a user for getting relief from sinus situations. More particularly the device may be used by a user require a cool mist or a warm mist for clearing nasal congestion or dry sinus situations or cooling down in warm/overheated situations. The device in the present invention uses a fine cool or warm vapor mist application through a face mask. Hot/Cold Personal Inhaler generates warm mist/cold mist delivery by creating an instant, fine mist that penetrates deep into a user's sinuses, nose and throat providing relief. The steam delivery is direct and targeted so maximum humidity is delivered directly to the nose, sinuses and throat right where it is most needed. Its soothing steam penetrates into the upper respiratory system to provide fast symptom relief for sinus congestion, allergies, colds/flu, cough, laryngitis, and discomfort from sore throat. The device also includes a face mask; a reservoir; an inhaler assembly including an ultrasonic transducer and a ceramic heater, and a power source; a switch; and indicators for indicating various states of the device.

It may be appreciated by a person with ordinary skill in the art, in light of and in accordance with the teachings of the present invention, that the heater employed in the device may be capable of providing the necessary heat as required by the device to produce a warm mist when required by a user. Suitable examples of heaters may include, but not be limited to, standard Resistance Wire, Positive Temperature Coefficient (PTC) or Ceramic heater technologies and the like, without departing from the scope and meaning of the present invention. In one embodiment, the heater may be a tubular heater.

It may be appreciated by a person with ordinary skill in the art, in light of and in accordance with the teachings of the present invention, that the ultrasonic transducer employed in the device may be capable of converting a fluid to a mist having a required particle size as required by the device to produce a warm mist or a cool mist when required by a user. Suitable examples of ultrasonic transducer may include, but not be limited to, a standard ultrasonic transducer, an ultrafine sonic transducer, ultrafine medical grade sonic transducer, and the like. The function of the ultrasonic transducer is to produce and deliver controlled ultra-fine particles of mist or fog in the inhaler for inhalation by a user. In one embodiment, the ultrasonic transducer is an ultrafine sonic transducer.

The ultrasonic mist generator comprises a piezoelectric-based ultrasonic transducer; a fixed or removable liquid reservoir or tank; a wick tube; a manifold including a spray nozzle/ultrasonic nebulizer with uniformly placed holes. The piezoelectric-based ultrasound transducer works similarly to an ultrasound humidifier. The transducer provides a means to produce large amounts of very fine water mist that is used for maximum absorption. The small drops generated by the ultrasonic transducer behave more like a gas, evenly moistening the nasal pathway and enabling the drops to be better absorbed with the airflow while breathing.

In various embodiments, the reservoir may be used to store water or other required fluid. For an easy explanation and consistency, water is considered as the fluid/liquid stored in the reservoir, throughout the detailed description. In one embodiment, the reservoir is removably attached to the personal inhaling device. In another embodiment, the reservoir may be fixed to the personal inhaling device. In one embodiment, the reservoir is provided with a provision to check a level of a fluid in the reservoir. It may be appreciated by a person with ordinary skill in the art, in light of and in accordance with the teachings of the present invention, that the reservoir may include different provisions to check the water level, such as a clear transparent area to act as a window to view the water level, an electronic digital display, a gauge system, and the like, without departing from the meaning and scope of the present invention. In one embodiment, the reservoir may include an indicator to indicate a level of liquid in the reservoir. The indicator may operate in a pre-determined manner to indicate the level of liquid in the reservoir. In one embodiment, the reservoir may include a unique angled water tank that is positioned to allow a user to angle back or forward the hand-held inhaler body for their personal optimum ergonomic angle.

Under operation, the delivery system of the ultrasonic transducer employs the wick tube to supply water from the reservoir to the transducer. The transducer utilizes and vibrates its metal disc and wires to generate a sonic mist and injects the mist into the manifold. From the manifold, the spray nozzle produces a fine spray of mist into the face mask which may then be inhaled by a user using the inhaling device. In one embodiment, where the user is using a cool mode of the inhaling device the cool mist is directly provided to the user through the face mask. In another embodiment, where the user is using a hot mode of the inhaling device the heater functions along with the ultrasonic transducer to provide a warm mist to the user through the face mask.

In an embodiment, the water supply system for the mist generator is a very small detachable/spring plunger release similar to mini-ultrasonic personal humidifiers (1.0 to 4.5 ounces depending on desired run time between refills). In another embodiment, the water supply system is in the form of a one-way valve. The wick tube pushes the valve open when the water tank is mounted on the hair styling tool. The valve arrangement for water supply is explained in details in the following figures.

In an embodiment, the present invention also provides potential in the apparatus to add customized personal scents to the cool or warm mist exiting from the inhaling device. In one embodiment, a receptacle may be placed in contact with the heater. A scented pad may be placed in the receptacle. A scent from the scented pad in the receptacle in contact with the heater may be released into the exiting heated warm mist.

Further, the device also has different input/output control modules to control the operation of the personal inhaling device. Different control modules may include and are not limited to Switch ON/OFF cool mode, Switch ON/OFF hot mode, mist flow output control, mist temperature output control, indicators in the device for indicated in a pre-determined manner the switch ON position in the cool mode, switch ON position in the hot mode, the switch OFF position, a level of charge of the power source, a level of the liquid in the reservoir, and the like. It may be appreciated by the person ordinarily skilled in the art that the input/output control module may be of different types, such as touch input, button inputs, scrolling buttons, LCD display, light emitting diode (LED) lights, and others, without departing from the meaning and scope of the present invention. In one embodiment, the indicators are LEDs.

Figure 1:
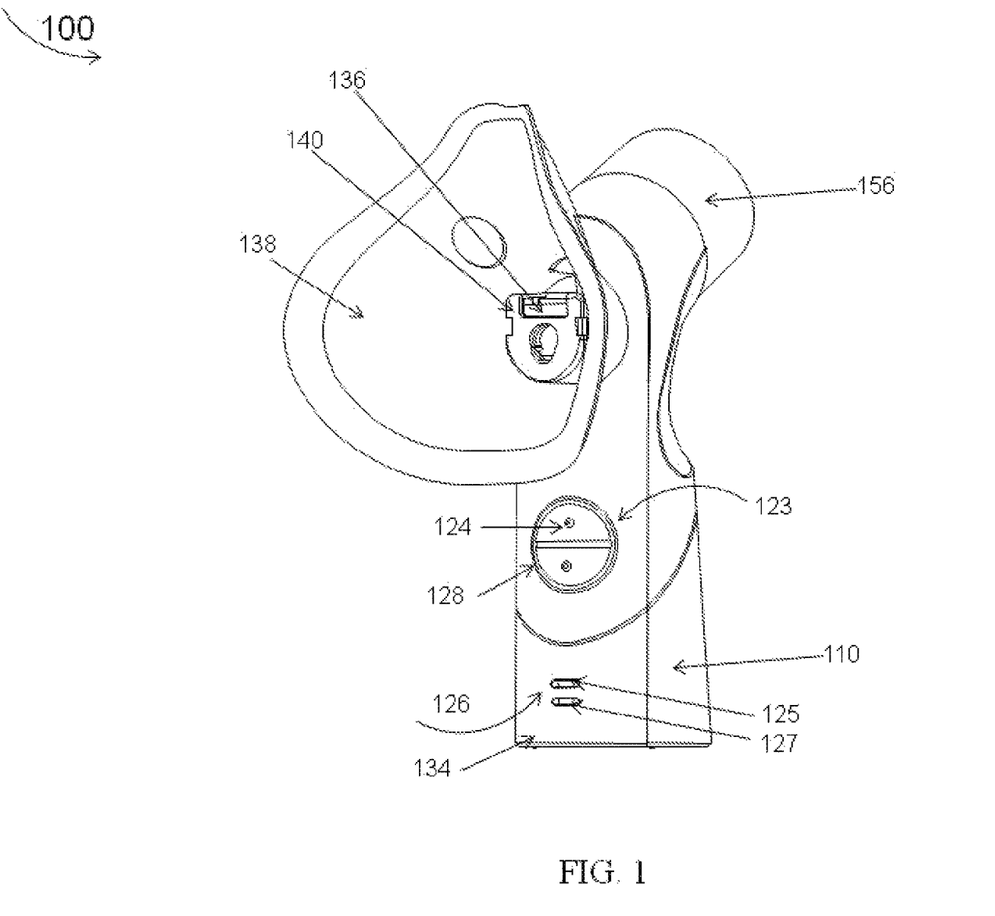
FIG. 1 illustrates a three-dimensional front view of the personal inhaling device, in accordance with an embodiment of the present invention.

Referring to FIG. 1 is illustrated a three-dimensional front view of the personal inhaling device 100, in accordance with an embodiment of the present invention. The personal inhaling device 100 includes a back-cover A 110, a reservoir 156, a face-mask 138, a receptacle for a scented pad 136, and a cover nozzle 140 for a heater (not shown in figure). The personal inhaling device 100 also includes a switch 123. The switch 123 includes a cover button 124. The switch 123 also includes a first indicator 128. In one embodiment, the first indicator is an LED light. In one embodiment, the first indicator is an LED light in the form of a ring that encircles the switch 123. The LED light changes color in a pre-determined manner to indicate various states of the device as provided, in one exemplary embodiment, in Table 1 hereinbelow. In the front view is also shown a second indicator 126. The second LED indicator 126, in one embodiment, is an LED light. In one embodiment, the second indicator indicates a level of charging of the power source. In one embodiment, the second indicator may include a first light emitting diode 125 and a second light emitting diode 127, wherein the first light emitting diode and the second light emitting diode indicate the level of charging of the power source in a pre-determined manner. The LED lights change color in a pre-determined manner to indicate various states of the device as provided, in one exemplary embodiment, in Table 1 hereinbelow. The device also includes a front cover 134.

Figure 2:
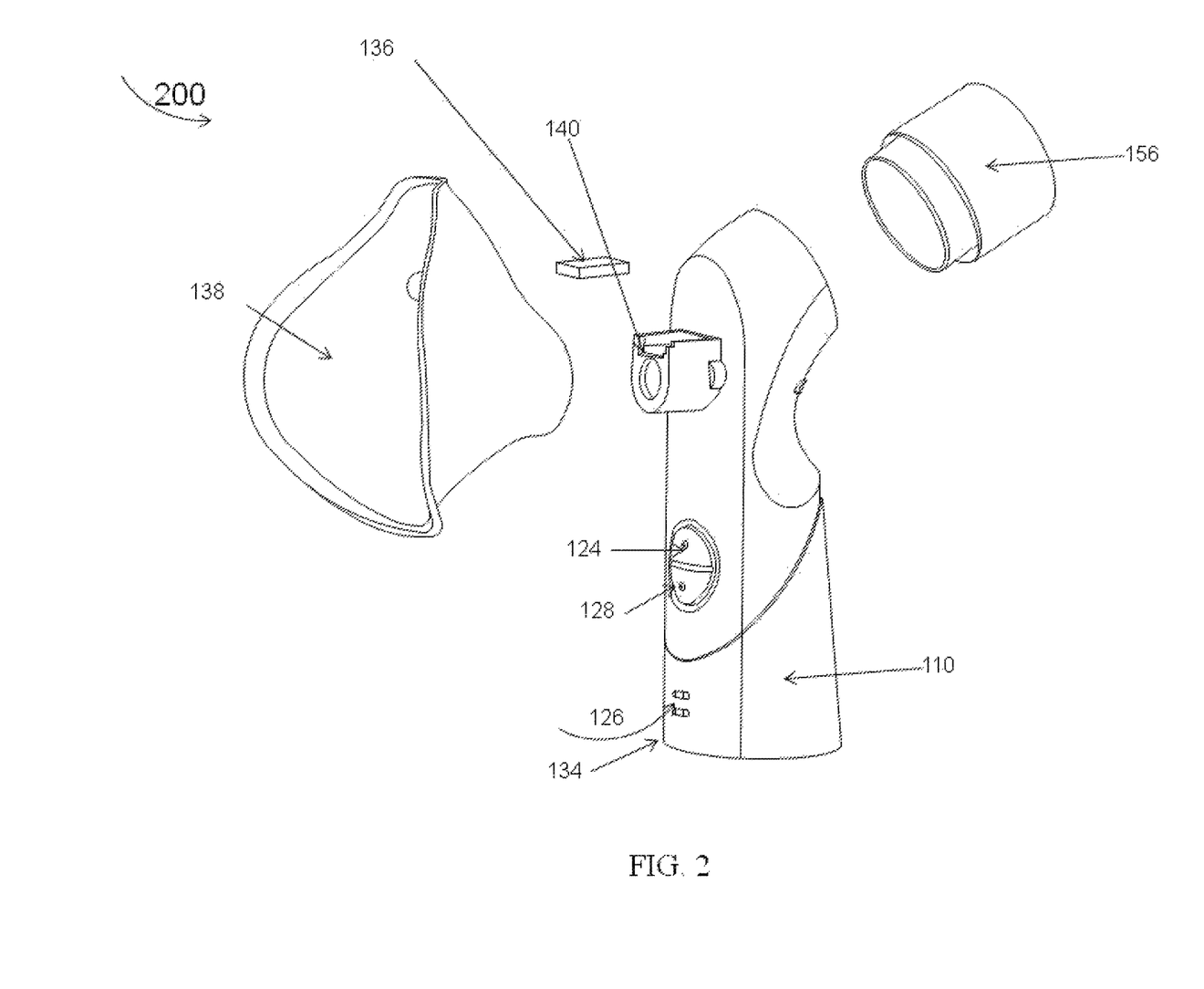
FIG. 2 illustrates an exploded view of the front side of the personal inhaling device, in accordance with an embodiment of the present invention.

Referring to FIG. 2 is provided an exploded view of the front side of the personal inhaling device 200, in accordance with an embodiment of the present invention. The view shows the four removable parts in the device, i.e., the face mask 138, the receptacle 136, the reservoir 156, and the portion (not numbered in figure) including the heater, ultrasonic transducer, switches etc. . . . . . A heater (not shown in figure), a heater cover 140, a receptacle for a scented pad 136 and the ultrasonic transducer (not shown in the figure) are arranged in the personal inhaling device 200. The personal inhaling device employs a one-way valve arrangement for allowing water supply from the reservoir 156 to the ultrasonic transducer via the wick tube. When the reservoir 156 is mounted on the personal inhaling device, the valve is left open. Whereas, when the reservoir 156 is dismantled from the personal inhaling device, the valve closes and discontinues the water supply avoiding any water leakage. The personal inhaling device 200 also includes a switch 123. The switch 123 includes a cover button 124. The switch 123 also includes a first indicator 128. In one embodiment, the first indicator is an LED light. In one embodiment, the first indicator is an LED light in the form of a ring that encircles the switch 123. The LED light changes color in a pre-determined manner to indicate various states of the device as provided, in one exemplary embodiment, in Table 1 herein below. In the front view is also shown a second indicator 126. The second LED indicator 126, in one embodiment, is an LED light. In one embodiment, the second indicator indicates a level of charging of the power source. In one embodiment, the second indicator may include a first light emitting diode 125 and a second light emitting diode 127, wherein the first light emitting diode and the second light emitting diode indicate the level of charging of the power source in a pre-determined manner. The LED lights change color in a pre-determined manner to indicate various states of the device as provided, in one exemplary embodiment, in Table 1 herein below. The device also includes a front cover 134.

Figure 3:
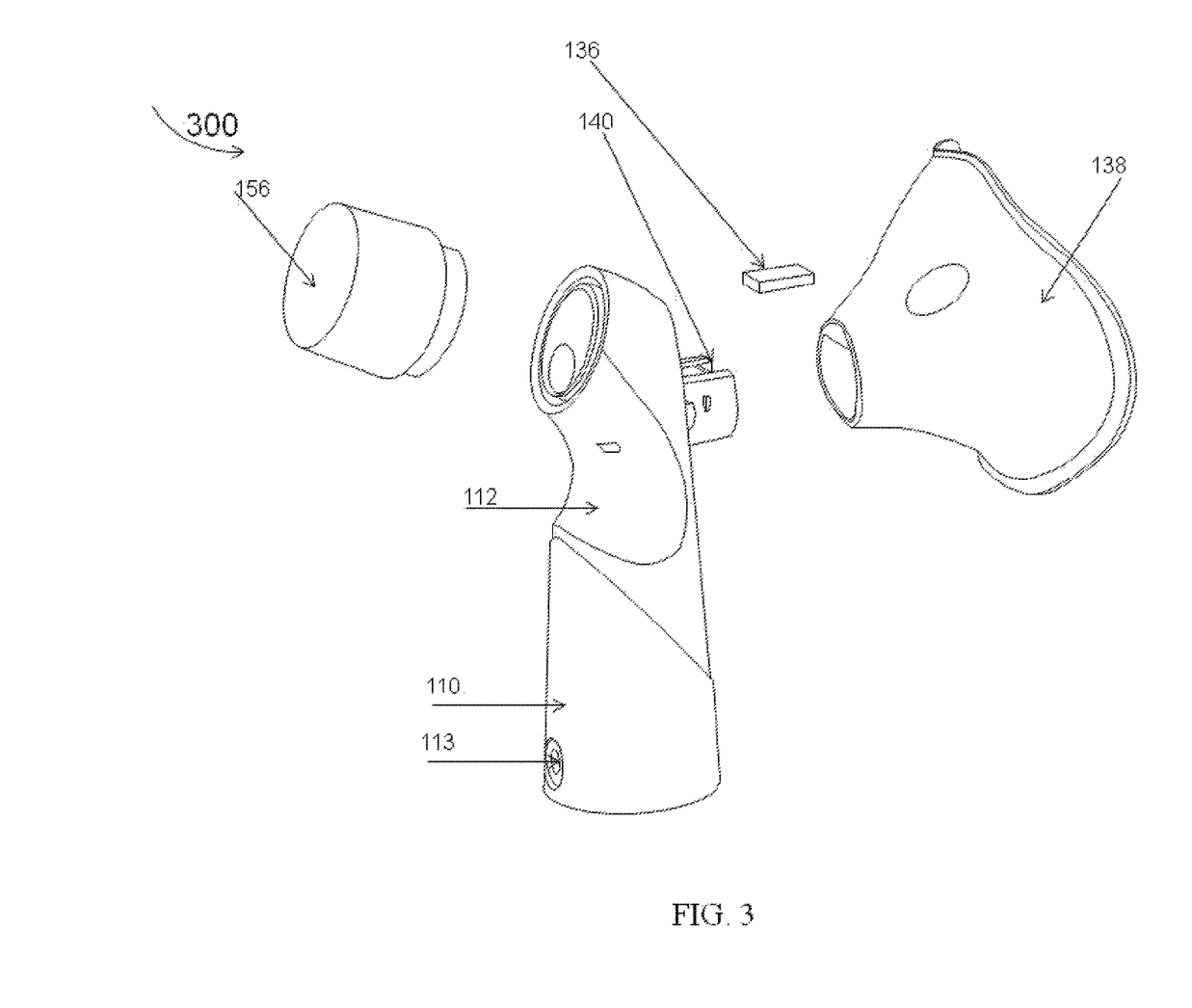
FIG. 3 illustrates an exploded view of the back side of the personal inhaling device, in accordance with an embodiment of the present invention.

Referring to FIG. 3 is illustrated an exploded view of the back side of the personal inhaling device, in accordance with an embodiment of the present invention. A heater (not shown in figure), a heater cover 140, a receptacle for a scented pad 136 and the ultrasonic transducer (not shown in the figure) are arranged in the personal inhaling device 300. The personal inhaling device employs a one-way valve arrangement for allowing water supply from the reservoir 156 to the ultrasonic transducer via the wick tube. When the reservoir 156 is mounted on the personal inhaling device, the valve is left open. Whereas, when the reservoir 156 is dismantled from the personal inhaling device, the valve closes and discontinues the water supply avoiding any water leakage. The personal inhaling device 300 also includes a cover back 110, a cover back 112, and a power supply port 113.

Figure 4:
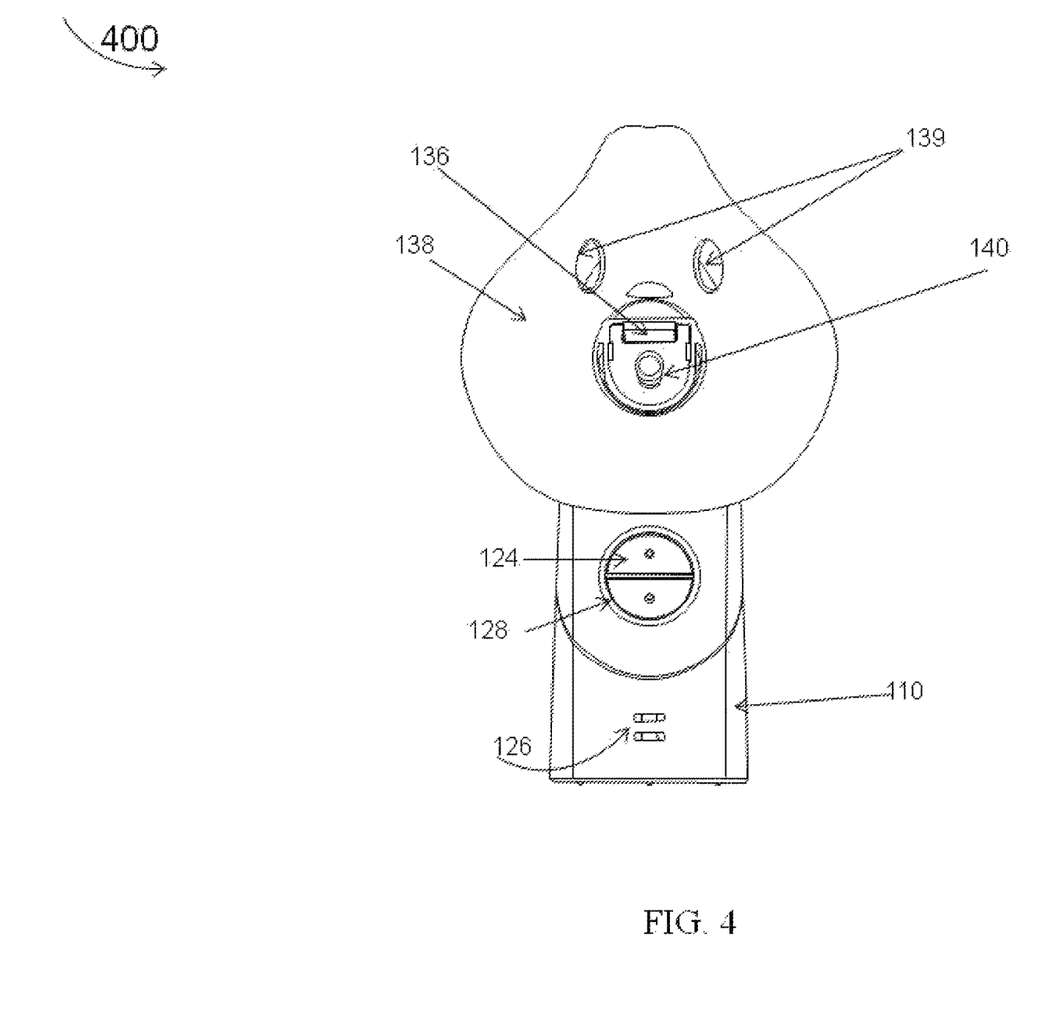
FIG. 4 illustrates a two-dimensional front view of the personal inhaling device, in accordance with an embodiment of the present invention.

Referring to FIG. 4 is illustrated a two-dimensional front view of the personal inhaling device, in accordance with an embodiment of the present invention. The view 400 shows vents 139 in the face mask 138, a heater cover 140, and a receptacle for a scented pad 136. The view 400 also shows the personal inhaling device 400 also includes a cover button 124 for covering a switch, a first indicator 128, a second indicator 126, and a cover back A 110.

Figure 5:
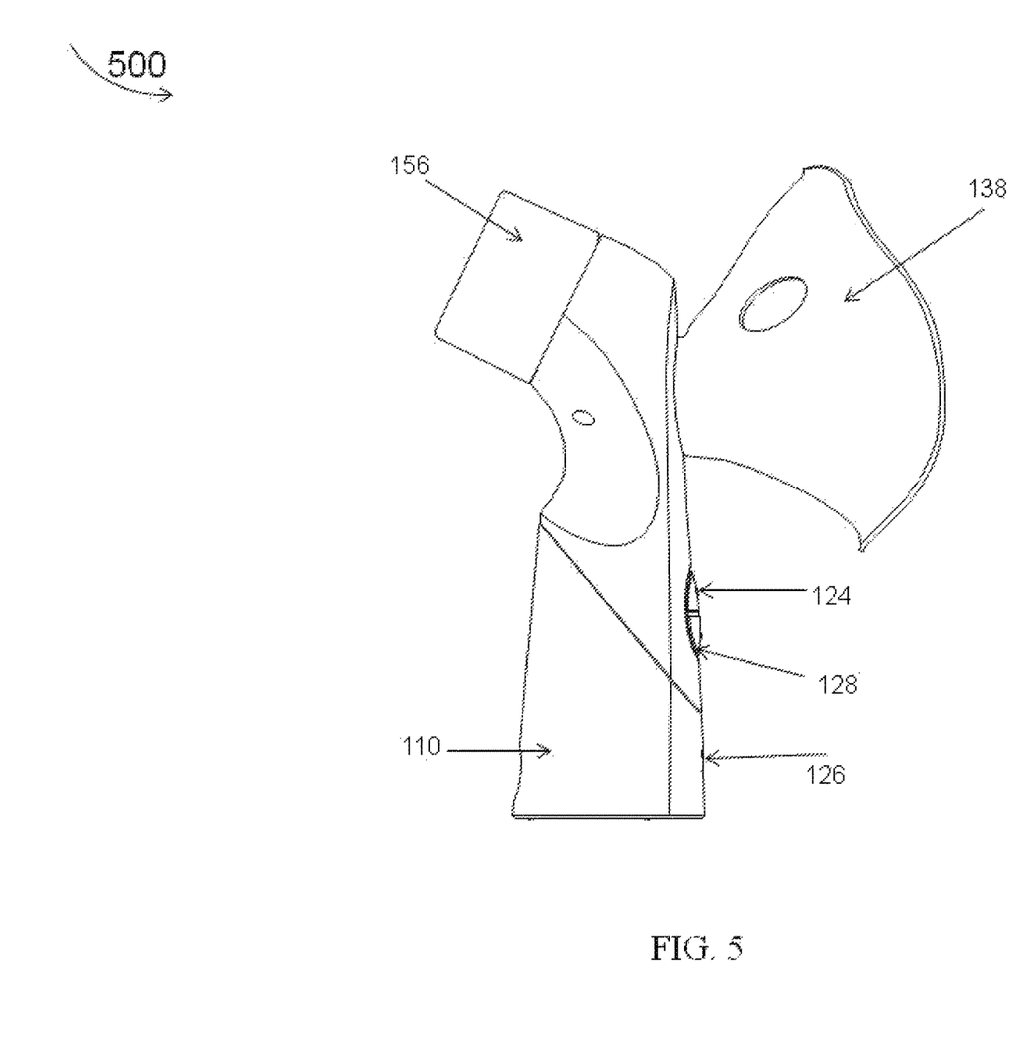
FIG. 5 illustrates a two-dimensional side view of the personal inhaling device, in accordance with an embodiment of the present invention.

Referring to FIG. 5 is illustrated a two-dimensional side view 500 of the personal inhaling device, in accordance with an embodiment of the present invention. The view 500 shows vents in the face mask 138, and a reservoir 156. The view 500 also includes a cover button 124 for covering a switch, a first indicator 128, a second indicator 126, and a cover back A 110.

Figure 6:
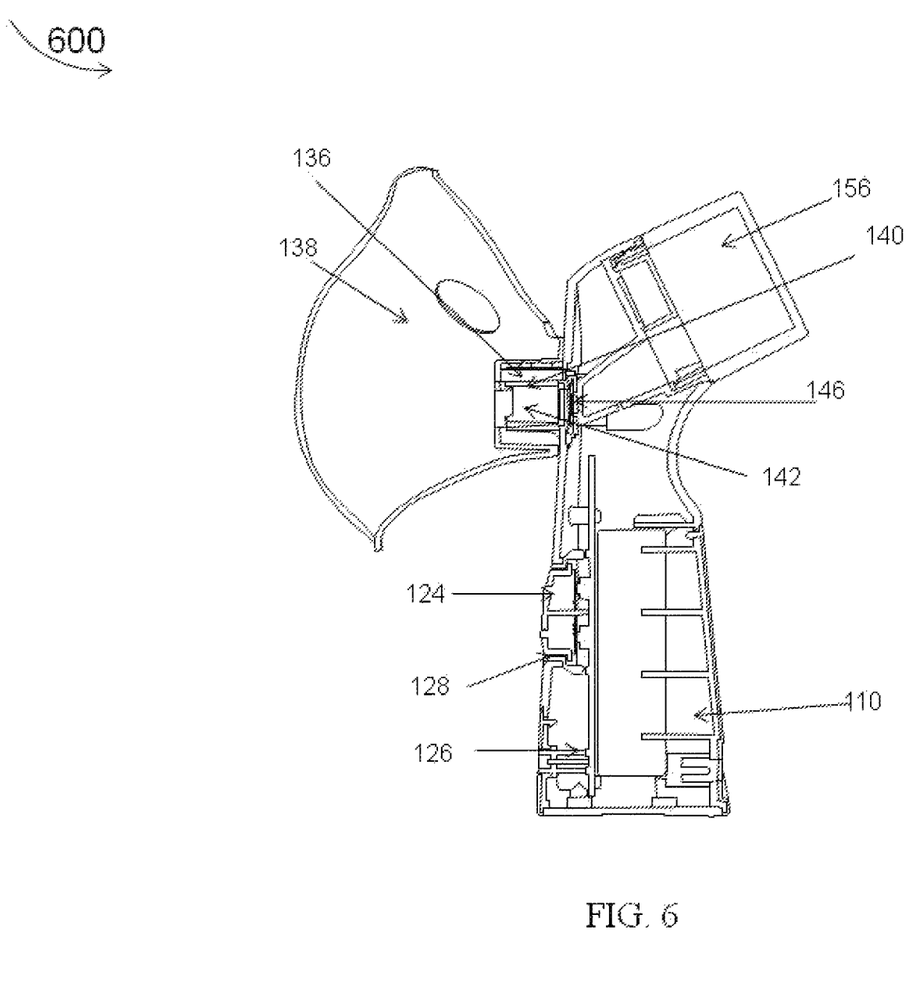
FIG. 6 illustrates a two-dimensional cross-sectional view of the personal inhaling device, in accordance with an embodiment of the present invention.

Referring to FIG. 6 is illustrated a two-dimensional cross-sectional view 600 of the personal inhaling device, in accordance with an embodiment of the present invention. The view 600 shows vents in the face mask 138, a receptacle for a scented pad 136, a cover 140 for a heater 142, a nebulizer 146, and a reservoir 156. The view 600 also includes a cover button 124 for covering a switch, a first indicator 128, a second indicator 126, and a cover back A 110.

Figure 7:
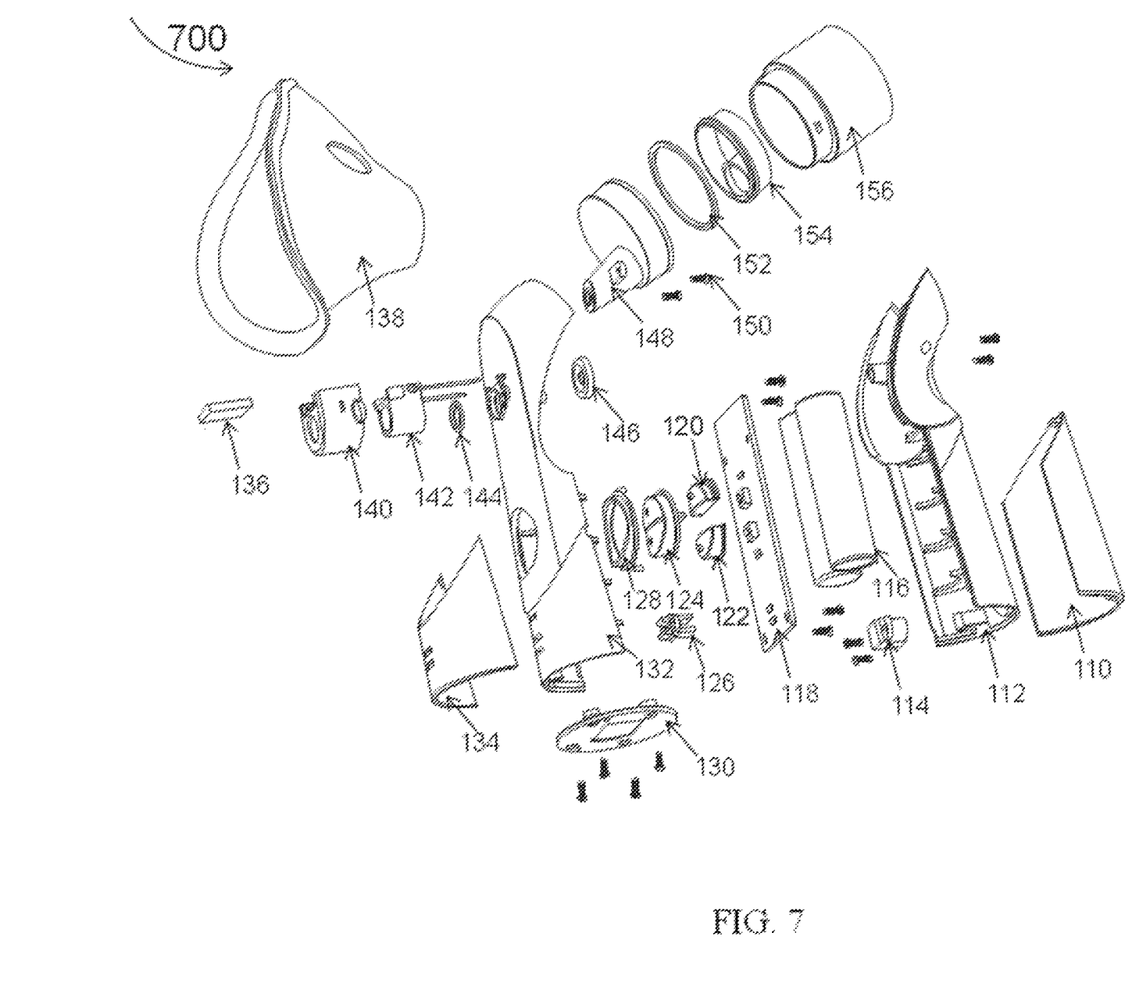
FIG. 7 illustrates a detailed exploded view of the personal inhaling device, in accordance with an embodiment of the present invention.

Referring to FIG. 7 is illustrated a detailed exploded view 700 of the personal inhaling device, in accordance with an embodiment of the present invention. In view 700 the personal inhaling device, in one exemplary embodiment, shows a cover back A 110, a cover back 112, a power port 114 (may also be at time referred to as a DC jack), batteries 116, a PCBA 118 (which controls the operations of the device i.e., heating, functioning of transducer, functioning of indicators, etc.), inside switch for switching on cool mode 120 (first portion of switch which is also the upper portion of the switch), inside switch for switching on hot mode 122 (second portion of switch which is also the lower portion of the switch), a cover for the switch 124, first indicator 128, second indicator 128, a base cover for the device 130, a front cover 132, a front cover A 134, a receptacle for a scented pad 136, a face mask 138, a nozzle cover 140 to cover the heater, a heater 142, a nylon ring 144, an atomizer/nebulizer 146, a reservoir base 148, a screw 150, a seal ring 152, portion providing reservoir capacity 154, and a reservoir 156. The reservoir 156 includes a third indicator (not shown in figure). It may be appreciated by a person with ordinary skill in the art, in light of and in accordance with the teachings of the present invention, that as discussed hereinabove the indicators may be of any convenient form, type, shape, color, etc. so as to be able to indicate the different states of the personal inhaling device in a pre-determined manner, i.e., the switch ON position in the cool mode, switch ON position in the hot mode, the switch OFF position, a level of charge of the power source, and a level of the liquid in the reservoir.

In one embodiment, the indicators are LEDs. In an exemplary embodiment, the first indicator 128 surrounding switch 123 may be in the form of a ring. In an exemplary embodiment, the ring is illuminated in blue color in the cool mode, in red color in the warm mode, and is colorless in the switched off state. In an exemplary embodiment, the second indicator 126 indicates a level of charging of the power source. In an exemplary embodiment, the second indicator includes a first light emitting diode 125 and a second light emitting diode 127, wherein the first light emitting diode 125 and the second light emitting diode 127 indicate the level of charging of the power source in a pre-determined manner. In an exemplary embodiment, the first and the second LED flash together in purple color in low battery condition when the cord is unplugged; the first and the second LED switch to green color when the power cord is plugged in; the first and the second LED flash in green color when the battery starts charging; the first green LED is solid, and the second green LED is blinking when the battery is half charged; and the first and second LEDs are solid when the battery is fully charged. In one embodiment, a third indicator provides illumination in the reservoir to enable a user to check the water level. In exemplary embodiments, the third indicator may change to blue color when the device is operating in the cool mode, may change to red color when the device is operating in the hot mode, and may change to purple color when water level is low in the reservoir.

Table 1 summarizes the indicator behavior in the various states of the personal inhaling device.

TABLE 1

| LED COLOR | TANK LED | BUTTON RING LED | UPPER LED INDI-CATOR | LOWER LED INDI-CATOR | STATUS |
|---|---|---|---|---|---|
| LED COLOR | Blue | Blue | OFF | Blue | Cool Mist Min |
| LED COLOR | Blue | Blue | Blue | Blue | Cool Mist Max |
| LED COLOR | Red | Red | OFF | Red | Warm Mist Low |
| LED COLOR | Red | Red | Red | Red | Warm Mist High |
| LED COLOR | OFF | OFF | OFF | Green Flash | Battery Charge To 1%-49% |
| LED COLOR | OFF | OFF | Green Flash | Green Solid | Battery Charge To 50%-99% |
| LED COLOR | OFF | OFF | Green Solid | Green Solid | Battery Charge to Full |
| LED COLOR | OFF | OFF | Purple | Purple | Low Water |
| LED COLOR | OFF | OFF | Purple (Both Flash) | Purple (Both Flash) | |

In one embodiment, the heater is a tubular heater 142 placed in the outlet nozzle of the ultrasonic transducer 146. The ultrasonic mist may be converted into and delivered as a warm mist in hot mode and may be delivered as a cool mist in the cool mode, i.e., the heater switch OFF mode. Further, the heated nozzle may offer different heat levels for user desired comfort. View 700 shows a switch 123 (not indicated in figure) covered by a switch cover 124. The switch is used to turn the device to a switch ON position or a switch OFF position. In the switch ON position the device is activated to function in a plurality of modes. In one exemplary embodiment, the plurality of modes comprise a cool mode and a hot mode. The switch 123 includes a first portion 120 and a second portion 122. The first portion 120 allows a user to operate the personal inhaling device in a cool mode and the second portion 122 allows a user to operate the personal inhaling device in a hot mode. The device also provides a means for adjusting flow rates in the cool mode of the personal inhaler device and a means for adjusting temperature and flow rates in the hot mode of the personal inhaler device. The means for adjustment in the hot mode comprises pressing the second portion 122 of the switch once to provide a low temperature and a low output hot mist; the means comprises pressing a second portion 122 of the switch twice to provide a higher temperature and a high output hot mist; and the means comprises pressing the second portion 122 of the switch thrice to turn the device to the switch OFF position. The means for adjustment in the cool mode comprises pressing the first portion 120 of the switch once to provide a low output cool mist; pressing the first portion 120 of the switch twice to provide a high output cool mist; and pressing the first portion of the switch thrice to turn the device to the switch OFF position. In one embodiment, the switch may be in the form of a see saw button, where the first portion may be pressed for setting off a cool mist and the second portion may be pressed for setting off a warm mist. In exemplary embodiments, the cool mist has an operational time in a range of from about 30 minutes to about 35 minutes for about 100 milliliters of liquid from a reservoir in the device, and the warm mist has an operational time in a range of from about 20 minutes to about 25 minutes; the warm mist at a low output has a temperature in a range of about 95 degree Fahrenheit to about 97 degree Fahrenheit at about an output of about 15 millimeters or milliliters, and the warm mist at a high output has a temperature in a range of about 105 degree Fahrenheit to about 107 degree Fahrenheit at about an output of about 15 millimeters or milliliters.

In one embodiment, the device has a power source. The device is capable of being operated with a low voltage AC to DC corded adapter and/or rechargeable DC batteries, or only with battery using disposable batteries or rechargeable batteries, with a low voltage AC to DC adapter with no batteries. In one embodiment, the device may be operated using rechargeable batteries 116 as shown in view 700. View 700 also shows a DC jack 114, such that the device may be operated as a corded device as the batteries recharge in the background.

In one embodiment, as described herein the face mask used in the device is vented. The use of an ultrafine sonic transducer creates a much finer water partial size in combination with a tubular heater that warms the exiting mist, and in combination with a vented face mask that pulls a cool air stream in to surround the heated warm mist emission. This principal is similar to that of the fan jet aircraft engines that use a cool air surround to accelerate the speed of hot air flow (Bernoulli's principle—Computer Definition. An increase in the velocity of a fluid that is accompanied by a decrease of pressure. Swiss scientist, Daniel Bernoulli (1700-1782), demonstrated that, in most cases, the pressure in a liquid or gas decreases as the liquid or gas moves faster.

In one embodiment, the heater 142 (in a tubular form) is placed directly in front of the ultrasonic transducer 146. This arrangement enables the device to set various heat levels to the exiting warm mist. Accordingly, in one embodiment, the ultrasonic transducer 146 i.e., the nebulizer in combination with the heater 142 is capable of warming an exiting mist from the reservoir 156 in the device to form a heated warm mist.

In one embodiment, the vents on the face mask are designed to pull in a cold air stream from surrounding environment to surround the heated warm mist. The receptacle 136 is placed directly over the heater 142. A scented pad may be placed in the receptacle 136. A scent from the scented pad in the receptacle in contact with the heater may be released into the exiting heated warm mist. The device may also include a slot below the heater to collect condensed vapors. The slot may in the form of a special tapered slot in the bottom of the heater tube to collect any condensation to drain forward into exiting air stream for evaporation.

It may be appreciated by a person with ordinary skill in the art, in light of and in accordance with the teachings of the present invention, that this technology may be adapted into beauty care for skin/body moisturizing. Further, warm mist ultrasonic generation could be adapted in room or central HVAC systems, as the particulate size if very fine may be more easily absorbed in the room.

In various embodiments, the personal inhaling device offers various advantages. Firstly, the device has a small and compact design that may operates with or without a cord. Further the hot and cold mode of the device provides a user with a flexible choice of warm or cool sinus relief. Furthermore, the device offers an option of using scent pads for the hot mode operation. It may be appreciated by a person with ordinary skill in the art, in light of and in accordance with the teachings of the present invention, that unlike a table top warm mist device, the use of an ultra-fine sonic nebulizer that reduces the water partial size to approximately half that of standard steam or sonic mist generators, thus minimizing or eradicating moisture droplets on the face of the user or on the inside of the face mask. Standard ultrasonic nebulizers produce much larger water partial size that results in dripping and heavy condensation. The finer the mist, the easier it is for the sinus cavity to absorb the mist.

Since other modifications and changes varied to fit particular operating requirements and environments are apparent to those skilled in the art, the invention is not considered limited to the example chosen for purposes of disclosure, and covers all changes and modifications which do not constitute departures from the true spirit and scope of this invention.

Although the invention has been explained in relation to its preferred embodiment, it is to be understood that many other possible modifications and variations can be made without departing from the spirit and scope of the invention as herein described.

As one of ordinary skill in the art may appreciate, the example apparatus and method described herein can be modified. For example, certain modules/elements can be omitted, certain elements can be carried added, and other steps can be added. Although particular embodiments of the invention have been described in detail, it is understood that the invention is not limited correspondingly in scope, but includes all changes, modifications and equivalents coming within the spirit and terms of the claims appended hereto.

While the invention has been described in connection with what is presently considered to be the most practical and various embodiments, it is to be understood that the invention is not to be limited to the disclosed embodiments, but on the contrary, is intended to cover various modifications and equivalent arrangements included within the spirit and scope of the appended claims.

This written description uses examples to disclose the invention, including the best mode, and also to enable any person skilled in the art to practice the invention, including making and using any devices or systems and performing any incorporated methods. The patentable scope the invention is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A personal inhaling device comprising:
   a face mask, wherein the face mask comprises a vented face mask;
   an ultrafine sonic transducer;
   a heater;
   a reservoir; wherein a liquid for forming a warm mist and a cool mist is stored in the reservoir;

a rechargeable power source;

a switch, wherein the switch is used to turn the device to a switch ON position or a switch OFF position;

wherein the face mask is attached to the heater for pulling in a cold air stream from the surrounding environment to surround the warm mist thus maintaining temperature level and moisture level of the exiting mist;

wherein in the switch ON position the device is activated to function in a plurality of modes, wherein the plurality of modes comprise a cool mode and a hot mode;

wherein in the switch ON position the cool mode is activated by pressing a first portion of the switch; and wherein in the switch ON position the hot mode is activated by pressing a second portion of the switch;

wherein the switch ON position in the cool mode, switch ON position in the hot mode, the switch OFF position, a level of charge of the power source, a level of the liquid in the reservoir, are indicated in a pre-determined manner using a first indicator, a second indicator, and a third indicator in the device;

wherein the first indicator is configured to indicate the switch ON position in the cool mode, the switch ON position in the hot mode, and the switch OFF position; wherein the switch is configured to adjust the flow rates and temperatures in the hot mode by pressing the second portion of the switch twice to provide a higher temperature and a high output warm mist;

wherein the first indicator is a light emitting diode that is illuminated in a pre-determined manner to indicate the cool mode in the switch ON position, hot mode in the switch ON position, and in the switch OFF position of the device;

wherein the second indicator is configured to indicate the level of charge of the power source;

wherein the second indicator comprises a first light emitting diode and a second light emitting diode, wherein the first light emitting diode and the second light emitting diode indicate the level of charging of the power source in a pre-determined manner;

wherein the third indicator is configured to indicate a level of the liquid in the reservoir; wherein the reservoir comprises the third indicator, wherein the third indicator comprises a light emitting diode, wherein the third indicator indicates a liquid level in the reservoir in a pre-determined manner;

a means for providing the cool mist in the cool mode of the device, the means comprising the ultrafine sonic transducer forming the cool mist from fluid provided by the reservoir;

a means for providing the warm mist in the hot mode of the device, the means comprising the heater attached to the ultrafine sonic transducer, the ultrafine sonic transducer in combination with the heater warming an exiting mist from fluid provided by the reservoir to form the warm mist in the hot mode of the device;

wherein the warm mist has an operational time in a range of from about 20 minutes to about 25 minutes;

wherein the warm mist at a low output has a temperature in a range of about 95 degree Fahrenheit to about 97 degree Fahrenheit at about an output of about 15 milliliters;

wherein the warm mist at a high output has a temperature in a range of about 105 degree Fahrenheit to about 107 degree Fahrenheit at about an output of about 15 milliliters; and a means for providing a scented exiting warm mist; the means comprising a receptacle for a scented pad in contact with the heater configured to generate the scented exiting warm mist upon mixing with the exiting mist from fluid provided by the reservoir.

2. The device recited in claim 1, wherein the switch is surrounded by a first indicator.

3. The device recited in claim 1, wherein the first portion of the switch is an upper portion of the switch.

4. The device recited in claim 1, wherein the second portion of the switch is a lower portion of the switch.

5. The apparatus recited in claim 1, wherein the third indicator changes to purple color when the liquid level is low in the reservoir.

6. A method of using a personal inhaler device, comprising:

providing a power source which is able to power the personal inhaler device using a low voltage AC to DC corded adapter, or a plurality of rechargeable batteries;

providing a reservoir for storing liquid;

providing an ultra-fine mist transducer, operationally connected to the reservoir, configured to convert the stored liquid into a cool mist or into a warm mist;

providing the ultra-fine mist transducer configured to direct a flow of the cool mist or the warm mist into a vented face mask;

providing the vented face mask configured to fit on a human face and to enable inhaling by said human of the cool mist or the warm mist;

providing a heating system, sandwiched between the reservoir and the vented face mask, operationally connected to the mist transducer, and configured to providing the warm mist in a hot mode;

providing a switch which is able to turn the personal inhaler device to a switch ON position, or to a switch OFF position;

providing a printed circuit board assembly to control the personal inhaling device, which will be configured for:

A. causing the personal inhaling device in the switch ON position to function in a plurality of modes;

B. enabling the plurality of modes to comprise a cool mode and the hot mode;

C. adjusting the flow rates and temperatures in the hot mode by pressing a second portion of the switch once to provide a low temperature and a low output warm mist;

D. adjusting the flow rates and temperatures in the hot mode by pressing the second portion of the switch twice to provide a higher temperature and a high output warm mist;

E. directing the personal inhaling device to the switch OFF position by pressing the second portion of the switch thrice;

F. adjusting the flow rates in the cool mode by pressing a first portion of the switch once to provide a low output cool mist;

G. adjusting the flow rates in the cool mode by pressing the first portion of the switch twice to provide a high output cool mist; and H. adjusting the flow rates in the cool mode by pressing the first portion of the switch thrice to the personal inhaling device to the switch OFF position.

7. The method of using a personal inhaler device of claim 6, wherein:

said storing liquid in the reservoir is water.

8. The method of using a personal inhaler device of claim 6, wherein the vented face mask is configured for pulling in a cold air stream from surrounding environment to surround the warm mist and thereby maintaining temperature of the warm mist.

9. The method of using a personal inhaler device of claim 6, wherein the warm mist has an operational time in a range of from about 20 minutes to about 25 minutes.

10. The method of using a personal inhaler device of claim 6, wherein the warm mist at the low output has a temperature in a range of about 95 degrees Fahrenheit to about 97 degrees Fahrenheit at about an output of about 15 milliliters.

11. The method of using a personal inhaler device of claim 6, wherein the warm mist at the high output has a temperature in a range of about 105 degrees Fahrenheit to about 107 degrees Fahrenheit at about an output of about 15 milliliters.

12. The method of using a personal inhaler device of claim 6, wherein the cool mist has an operational time in a range of from about 30 minutes to about 35 minutes for about 100 milliliters of liquid from a reservoir in the device.

* * * * *